(12) United States Patent
Kawamura et al.

(10) Patent No.: US 11,841,373 B2
(45) Date of Patent: Dec. 12, 2023

(54) INFORMATION PROCESSING APPARATUS, METHOD FOR CONTROLLING INFORMATION PROCESSING APPARATUS, AND PROGRAM

(71) Applicant: CANON KABUSHIKI KAISHA, Tokyo (JP)

(72) Inventors: Hidetaka Kawamura, Yokohama (JP); Akihiro Taya, Yokohama (JP); Yutaka Yoshimasa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 220 days.

(21) Appl. No.: 16/896,690

(22) Filed: Jun. 9, 2020

(65) Prior Publication Data
US 2020/0408789 A1 Dec. 31, 2020

(30) Foreign Application Priority Data

Jun. 28, 2019 (JP) .................................. 2019-121955
Apr. 22, 2020 (JP) .................................. 2020-076006

(51) Int. Cl.
*G01N 15/00* (2006.01)
*G06N 20/00* (2019.01)
*G01N 35/00* (2006.01)

(52) U.S. Cl.
CPC ....... *G01N 35/00732* (2013.01); *G06N 20/00* (2019.01)

(58) Field of Classification Search
CPC ......................... G01N 35/00732; G06N 20/00
See application file for complete search history.

(56) References Cited

U.S. PATENT DOCUMENTS

| 5,553,616 | A  | * | 9/1996 | Ham | A61B 5/6826 |
|---|---|---|---|---|---|
| | | | | | 250/341.1 |
| 11,022,537 | B2 | * | 6/2021 | Otsuka | G01N 15/14 |
| 2009/0018804 | A1 | * | 1/2009 | Senyard | G16C 20/20 |
| | | | | | 703/2 |
| 2012/0089344 | A1 | * | 4/2012 | Wright | G06K 9/0053 |
| | | | | | 703/2 |

(Continued)

FOREIGN PATENT DOCUMENTS

| JP | 6-324029 A | 11/1994 |
|---|---|---|
| JP | 2006-177980 A | 7/2006 |
| JP | 2018-152000 A | 9/2018 |

OTHER PUBLICATIONS

Li X, Xie C, He Y, Qiu Z, Zhang Y. Characterizing the moisture content of tea with diffuse reflectance spectroscopy using wavelet transform and multivariate analysis. Sensors (Basel). 2012;12(7):9847-61. doi: 10.3390/s120709847. Epub Jul. 23, 2012. PMID: 23012574; PMCID: PMC3444132. (Year: 2012).*

(Continued)

*Primary Examiner* — Raymond L Nimox
(74) *Attorney, Agent, or Firm* — CANON U.S.A., INC. IP Division

(57) ABSTRACT

An apparatus includes an acquisition unit configured to acquire quantitative information on a test substance, the quantitative information being estimated by inputting, to a learning model, two or more pieces of spectral information selected from a plurality of pieces of spectral information on a sample containing the test substance and a foreign substance.

28 Claims, 16 Drawing Sheets

(56) References Cited

U.S. PATENT DOCUMENTS

| | | | |
|---|---|---|---|
| 2014/0183353 A1* | 7/2014 | Shimada | H01J 49/0036 |
| | | | 250/281 |
| 2017/0045441 A1* | 2/2017 | Nciri | G01J 3/10 |
| 2020/0049722 A1* | 2/2020 | Fryar-Williams | C12Q 1/6883 |
| 2020/0279408 A1* | 9/2020 | Osoekawa | G06N 3/04 |
| 2020/0292509 A1* | 9/2020 | Osoekawa | G01N 30/8693 |
| 2021/0201140 A1* | 7/2021 | Watanabe | G01N 21/274 |
| 2021/0319364 A1* | 10/2021 | Fujita | G06Q 10/04 |

OTHER PUBLICATIONS

Metin Akay, "Artificial Neural Networks for Spectroscopic Signal Measurement," in Nonlinear Biomedical Signal Processing, Fuzzy Logic, Neural Networks, and New Algorithms, IEEE, 2000, pp. 216-232, doi: 10.1109/9780470545362.ch9. (Year: 2000).*

Taiwei Lu and J. Lerner, "Spectroscopy and hybrid neural network analysis," in Proceedings of the IEEE, vol. 84, No. 6, pp. 895-905, Jun. 1996, doi: 10.1109/5.503145. (Year: 1996).*

* cited by examiner

INFORMATION PROCESSING APPARATUS, METHOD FOR CONTROLLING INFORMATION PROCESSING APPARATUS, AND PROGRAM

BACKGROUND OF THE INVENTION

Field of the Invention

The aspect of the embodiments relates to an information processing apparatus, a method for controlling the information processing apparatus, and a program.

Description of the Related Art

Spectral analysis is used extensively as a method for determining the concentrations and the amounts of specific constituents (hereinafter referred to as "test substance") contained in various samples. Spectral analysis allows acquiring information (spectral information) on the constituents of the sample from a signal obtained by detecting a response when the sample is stimulated. The spectral information includes the intensity, temperature, and mass of an electromagnetic wave including light, which characterize the stimulus and response, and the count value of fragments having a specific mass. The spectral analysis also includes recording the value of the mass of fragments produced by decomposition caused by using electronic collision as a stimulus to acquire information on the structure or the like.

The spectral analysis includes a method of analysis by separating a sample using a difference in three-dimensional size, electric charge, or hydrophobic or hydrophilic property among its constituents and then applying electromagnetic waves thereto. This is called separation analysis. High-performance liquid chromatography (HPLC) separates a test substance from the other substances (hereinafter referred to as "foreign substances") by optimizing the column type, mobile phase type, and analytical conditions, such as temperature and flow rate. Measuring the spectrum of the separated test substance allows determining the concentration and the amount. If separation from the foreign substances cannot be performed, peak separation using arithmetic processing can be tried.

Known peak separation methods include a method for separation using a base line (see FIG. 3), a method for vertical separation using a minimum value between peaks (see FIG. 4), and a method for separation by fitting an appropriate function, such as a Gaussian function using a method of least squares, described in Japanese Patent Laid-Open No. 6-324029 and No. 2006-177980. In FIGS. 3 and 4, the areas of the peaks are indicated by the hatch lines. The height of the peak is denoted by Y.

HPLC is often used to analyze biological samples. However, biological samples, such as urine and blood, can contain many foreign substances and unknown foreign substances originating from ingested materials. Therefore, HPLC needs an operator who is skilled in the study of separation conditions for separating the test substance from foreign substances, preprocessing, and the peak separation method.

Furthermore, samples used in analyzing the residual agricultural chemicals of food and environmental analysis can contain many foreign substances. This requires a method for analyzing a test substance in a sample easily and accurately without the need for preprocessing even for beginners.

Thus, to obtain quantitative information, such as the concentration or mass of the test substance, from spectral information, the known methods are preprocessing for obtaining foreign substances and arithmetic processing, such as peak separation. If an information processing apparatus capable of calculating quantitative information using a learning model based on spectral information on a sample containing a test substance is used, the test substance in the sample may be easily analyzed. However, it turned out that, if the sample contains a foreign substance having a peak overlapping with the peak of the test substance, the estimated accuracy of the quantitative information on the test substance in the sample decreases or the quantitative information itself cannot be calculated.

SUMMARY OF THE INVENTION

The aspect of the embodiments provides an apparatus for estimating quantitative information on the test substance even if the sample contains foreign substances having a peak overlapping with the peak of the test substance. The aspect of the embodiments also provides a method for controlling the apparatus, as well as a program.

In a first aspect of the embodiments, an apparatus includes an acquisition unit configured to acquire quantitative information on a test substance, the quantitative information being estimated by inputting, to a learning model, two or more pieces of spectral information selected from a plurality of pieces of spectral information on a sample containing the test substance and a foreign substance.

In a second aspect of the embodiments, a method includes acquiring quantitative information on a test substance, the quantitative information being estimated by inputting, to a learning model, two or more pieces of spectral information selected from a plurality of pieces of spectral information on a sample containing the test substance and a foreign substance.

Further features of the disclosure will become apparent from the following description of exemplary embodiments with reference to the attached drawings.

DESCRIPTION OF THE EMBODIMENTS

Figure 1:
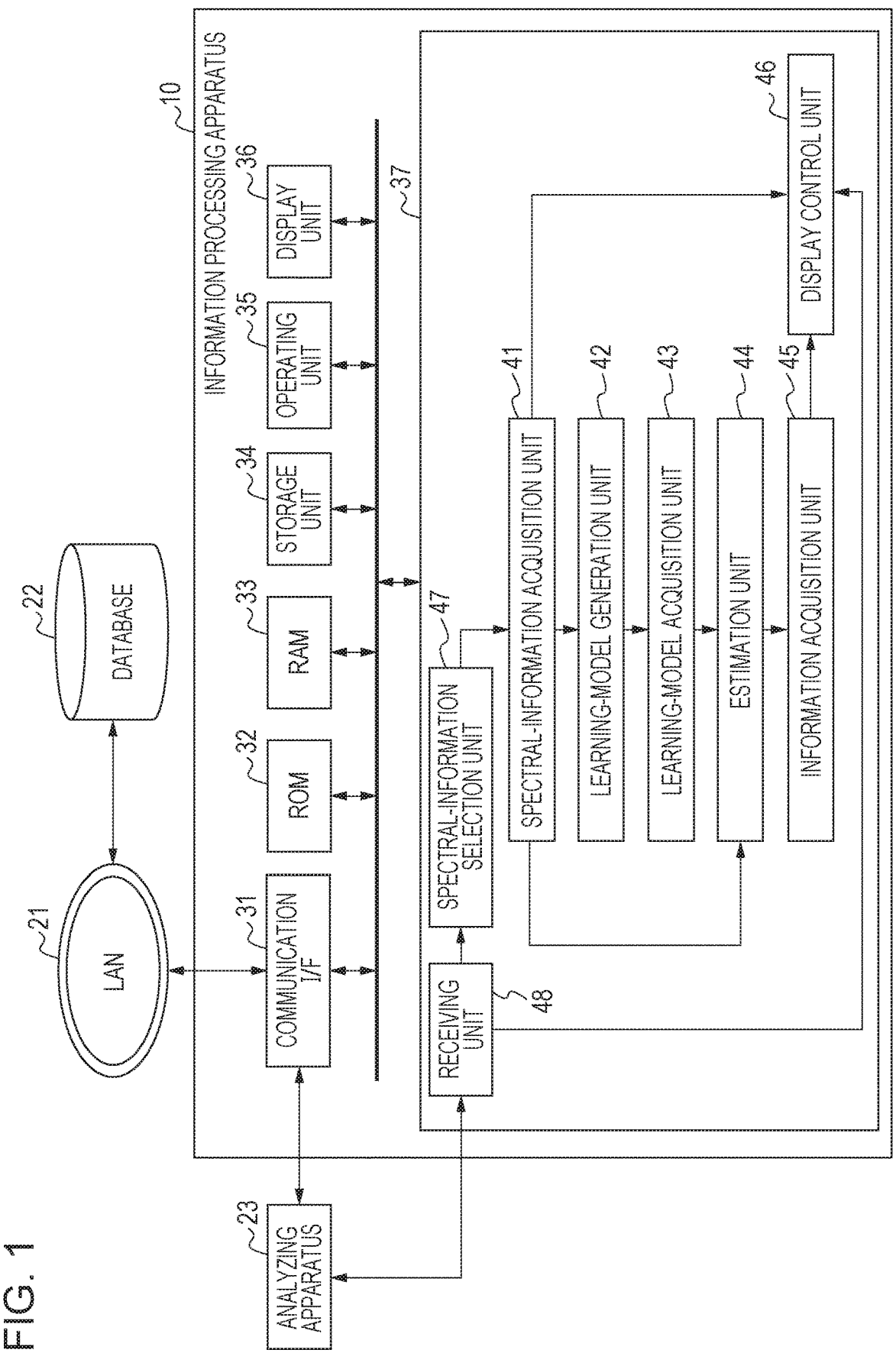
FIG. 1 is a diagram illustrating the overall configuration of an information processing system including an information processing apparatus according to an embodiment of the disclosure.

Embodiments of the disclosure will be described hereinbelow with reference to the drawings. However, the scope of the disclosure is not limited to the embodiments described below.

In the aspect of the embodiments, to accurately estimate quantitative information on a test substance, the amount of the test substance is calculated using a plurality of pieces of spectral information. The plurality of pieces of spectral information include spectral information obtained at different wavelengths. Even if peaks of a test substance and peaks of foreign substances overlap in one spectral information, so that it is difficult to estimate the amount of the test substance, the use of the plurality of pieces of spectral information may allow distinguishing the peaks of the test substance and the peaks of the foreign substances from each other by using another spectral information. This allows estimating the amount of the test substance. To use a plurality of pieces of spectral information as described above, it is important to select two or more pieces of spectral information with a spectrum selection unit of the information processing apparatus. The spectrum selection unit will be described below.

Sample

The sample in the present embodiment is a mixture containing multiple kinds of compound. In the present embodiment, the sample is a mixture containing a test substance and foreign substances. The constituents of the mixture may not be necessarily be specified. The mixture may contain an unknown constituent. For example, the mixture may be a biological mixture, such as blood, urine, or saliva, or food and drink. Since a biological sample includes a clue to determine the health of the sample provider, the analysis is medically valuable.

For example, vanillyl mandelic acid contained in urine is a marker for childhood cancer and is therefore useful in discovering a tumor. Creatinine contained in urine, if the amount of excretion can be estimated, indicates the condition of the renal function.

Test Substance

The test substance in the present embodiment is one or more known constituents contained in the sample. The test substance may be of at least one kind selected from a group consisting of protein, deoxyribonucleic acid (DNA), virus, fungi, water-soluble vitamins, fat-soluble vitamins, organic acids, fatty acids, amino acids, saccharides, agricultural chemicals, and environmental hormones.

Quantitative Information

Quantitative information in the present embodiment includes the amount of a test substance in the sample, the concentration of the test substance in the sample, and whether the test substance is present in the sample. Another quantitative information includes the ratio of the amount or the concentration of the test substance in the sample to the reference amount of the test substance, and the proportion of the amount or the concentration of the test substance in the sample.

Spectral Information

Spectral information in the present embodiment includes a chromatogram, a photoelectron spectrum, an infrared absorption spectrum (IR spectrum), a nuclear magnetic resonance spectrum (NMR spectrum), a fluorescence spectrum, a fluorescent X-ray spectrum, an ultraviolet-visible absorption spectrum (UV/Vis spectrum), a Raman spectrum, an atomic absorption spectrum, a frame emission spectrum, an emission spectrum, an X-ray absorption spectrum, an X-ray diffraction spectrum, a paramagnetic resonance absorption spectrum, an electron spin resonance spectrum, and a thermal-analysis spectrum.

Information Processing System and Information Processing Apparatus

An information processing system of the present embodiment will be described with reference to FIG. 1. FIG. 1 is a diagram illustrating the overall configuration of the information processing system including an information processing apparatus according to the present embodiment.

The information processing system includes an information processing apparatus 10, a database 22, and an analyzing apparatus 23. The information processing apparatus 10 and the database 22 are connected so as to communicate with each other via a communication means. In the present embodiment, the communication means is a local area network (LAN) 21. The information processing apparatus 10 and the analyzing apparatus 23 are connected by a communication means, such as a universal serial bus (USB) standard. The LAN may be a wired LAN, a wireless LAN, or a wide area network (WAN). The USB may be a LAN.

The database 22 manages spectral information obtained by analysis performed by the analyzing apparatus 23. The database 22 also manages a learning model (a learned model) generated by a learning-model generation unit 42, to be described below. The information processing apparatus 10 obtains the spectral information and the learning model managed by the database 22 via the LAN 21.

Learning Model

The learning model in the present embodiment is a regression learning model, which is generated by machine learning, such as deep learning. A model that is configured to perform appropriate prediction by learning using training data for a machine learning algorithm is hereinafter referred to as a learning model. There are various kinds of machine learning algorithm used as learning models. For example, deep learning using a neural network can be used. The neural network includes an input layer, an output layer, and a plurality of hidden layers. These layers are connected by a formula called an activation function. In using labeled training data (training data with an output corresponding to an input), the coefficients of the activation function are determined so as to satisfy the relation between the input and the output. Determining the coefficients using a plurality of pieces of training data allows creating a learning model with which an output corresponding to an input can be predicted with high accuracy.

Analyzing Apparatus

The analyzing apparatus 23 is an apparatus for analyzing samples and test substances. The analyzing apparatus 23 corresponds to an example of an analyzing unit. In the present embodiment, the information processing apparatus 10 and the analyzing apparatus 23 are connected so as to communicate with each other, as described above. Alternatively, the analyzing apparatus 23 may be provided in the information processing apparatus 10, or the information processing apparatus 10 may be provided in the analyzing apparatus 23. In another embodiment, the result of analysis (spectral information) is transferred from the analyzing apparatus 23 to the information processing apparatus 10 via a recording medium, such as a non-volatile memory.

The analyzing apparatus 23 of the present embodiment may be any analyzing apparatus that can obtain spectral information using a chemical analytical method or a physical analytical method. In the present embodiment, examples of the chemical analytical method include chromatography, such as liquid chromatography and gas chromatography, and capillary electrophoresis. Examples of the physical analytical method include photoelectric spectroscopy, infrared absorption spectroscopy, nuclear magnetic resonance spectroscopy, fluorescent spectroscopy, fluorescent X-ray spectroscopy, visible-ultraviolet absorption spectroscopy, Raman spectroscopy, an atomic absorption method, frame emission spectroscopy, emission spectroscopy, X-ray absorption spectroscopy, an X-ray diffraction method, electron spin resonance spectroscopy using paramagnetic resonance absorption or the like, and a thermo-analytical method.

For example, an apparatus using liquid chromatography includes a mobile-phase container, a feed pump, a sample injection port, a column, a detector, and an analog-to-digital (A/D) converter. Examples of the detector include an electromagnetic detector using ultraviolet light or infrared light, an electrochemical detector, and an ion detector. In this case, the spectral information obtained is the intensity of an output from the detector relative to time.

The information processing apparatus 10, includes, as its functional configuration, a communication interface (IF) 31, a read only memory (ROM) 32, a random access memory (RAM) 33, a storage unit 34, an operating unit 35, a display unit 36, and a control unit 37.

The communication IF 31 is implemented by a LAN card and a USB card, for example. The communication IF 31 is responsible for communication between an external device (for example the database 22 and the analyzing apparatus 23) and the information processing apparatus 10 via the LAN 21 and the USB. The ROM 32 is implemented by a non-volatile memory or the like and stores various programs. The RAM 33 is implemented by a volatile memory or the like and temporarily stores a variety of information. The storage unit 34 is implemented by, for example, a hard disk drive (HDD) and stores a variety of information. The operating unit 35 is implemented by, for example, a keyboard and a mouse, and inputs instructions from the user to the apparatus. The display unit 36 is implemented by, for example, a display, and displays a variety of information to the user. The operating unit 35 and the display unit 36 provide a function as a graphical user interface (GUI) under the control of the control unit 37.

Control Unit

The control unit 37 is implemented by, for example, at least one central processing unit (CPU), and coordinates and provides control of processing of the information processing apparatus 10. The control unit 37 includes, as its functional configuration, a receiving unit 48, a spectral-information selection unit 47, a spectral-information acquisition unit 41, a learning-model generation unit 42, a learning-model acquisition unit 43, an estimation unit 44, an information acquisition unit 45, and a display control unit 46.

Receiving Unit 48

The receiving unit 48 can acquire the result of analysis obtained by the analyzing apparatus 23, specifically, spectral information on the sample. The receiving unit 48 may acquire the result of analysis, that is, spectral information on the sample, from a database (the database 22 in FIG. 1) prepared in advance.

Spectral-Information Selection Unit 47

The spectral-information selection unit 47 acquires the result of analysis of samples containing a test substance and foreign substances, specifically, spectral information on a plurality of samples, from the analyzing apparatus 23 and selects at least two pieces of spectral information from the spectral information on the plurality of samples. Alternatively, the spectral-information selection unit 47 may acquire spectral information on a plurality of samples from the database 22 in which the result of analysis is stored in advance and may select at least two pieces of spectral information from the spectral information on the plurality of samples.

The spectral-information selection unit 47 also acquires spectral information on a plurality of test substances and selects at least two pieces of spectral information from the spectral information on the plurality of test substances. The spectral information on the test substances is spectral information in the case where the test substances are present in a single form. Here, the plurality of pieces of spectral information may be spectral information obtained at different measurement wavelengths. In acquiring spectral information at different wavelengths, the wavelengths used in obtaining spectral information selected from each of the spectral information on the sample and the test substance may be the same.

Spectral-Information Acquisition Unit 41

The spectral-information acquisition unit 41 acquires connected spectral information in which the spectral information on the sample and the spectral information on the test substance, selected by the spectral-information selection unit 47, are connected. The connected spectral information is information obtained by connecting the data on the plurality of spectra measured. For example, if a measurement wavelength can be selected in acquiring a spectrum, the connected spectral information is information obtained by combining a plurality of pieces of spectrum data obtained at a plurality of measurement wavelengths. The spectral-information acquisition unit 41 outputs the obtained connected spectral information on the sample to the estimation unit 44. The spectral-information acquisition unit 41 also outputs the obtained connected spectral information on the test substance to the learning-model generation unit 42.

Learning-Model Generation Unit 42

The learning-model generation unit 42 generates training data using the connected spectral information in which the plurality of pieces of spectral information on the test substance acquired by the spectral-information acquisition unit 41 are connected. The learning-model generation unit 42 executes deep learning using the training data to generate a learning model. A detailed description of the generation of the training data and the generation of the learning model will be described below. The learning-model generation unit 42 outputs the generated learning model to the learning-model acquisition unit 43. The learning-model generation unit 42 may output the generated learning model to the database 22.

Learning-Model Acquisition Unit 43

The learning-model acquisition unit 43 acquires the learning model generated by the learning-model generation unit 42. In the case where the learning model is stored in the database 22, the learning-model acquisition unit 43 obtains the learning model from the database 22. The learning-model acquisition unit 43 outputs the obtained learning model to the estimation unit 44.

Estimation Unit 44

The estimation unit 44 causes the learning model acquired by the learning-model acquisition unit 43 to estimate quantitative information on the test substance contained in the sample by inputting to the learning model the connected spectral information in which the spectral information on the sample is combined. The estimation unit 44 outputs the estimated quantitative information to the information acquisition unit 45. The estimation unit 44 corresponds to an example of an estimation unit that estimates quantitative information on the test substance by inputting sample spectral information to the learning model.

Information Acquisition Unit 45

The information acquisition unit 45 acquires the quantitative information estimated by the learning model. In other words, the information acquisition unit 45 corresponds to an example of an information acquisition unit that acquires quantitative information on the test substance, which is estimated by inputting connected spectral information on the sample containing the test substance and foreign substances to the learning model. The information acquisition unit 45 outputs the acquired quantitative information to the display control unit 47.

Display Control Unit 46

The display control unit 46 controls the display unit 36 to display the quantitative information acquired by the information acquisition unit 45. The display control unit 47 corresponds to an example of a display control unit.

At least part of the components of the control unit 37 may be each implemented as an independent device or may be implemented as software that implements its function. In this case, the software that implements the function may be operated on a server via a network, like cloud. In the present embodiment, the individual components are implemented by software in a local environment.

The configuration of the information processing system illustrated in FIG. 1 is given for illustrative purpose only. For example, the storage unit 34 of the information processing apparatus 10 may have the function of the database 22 and may store a variety of information.

Figure 2:
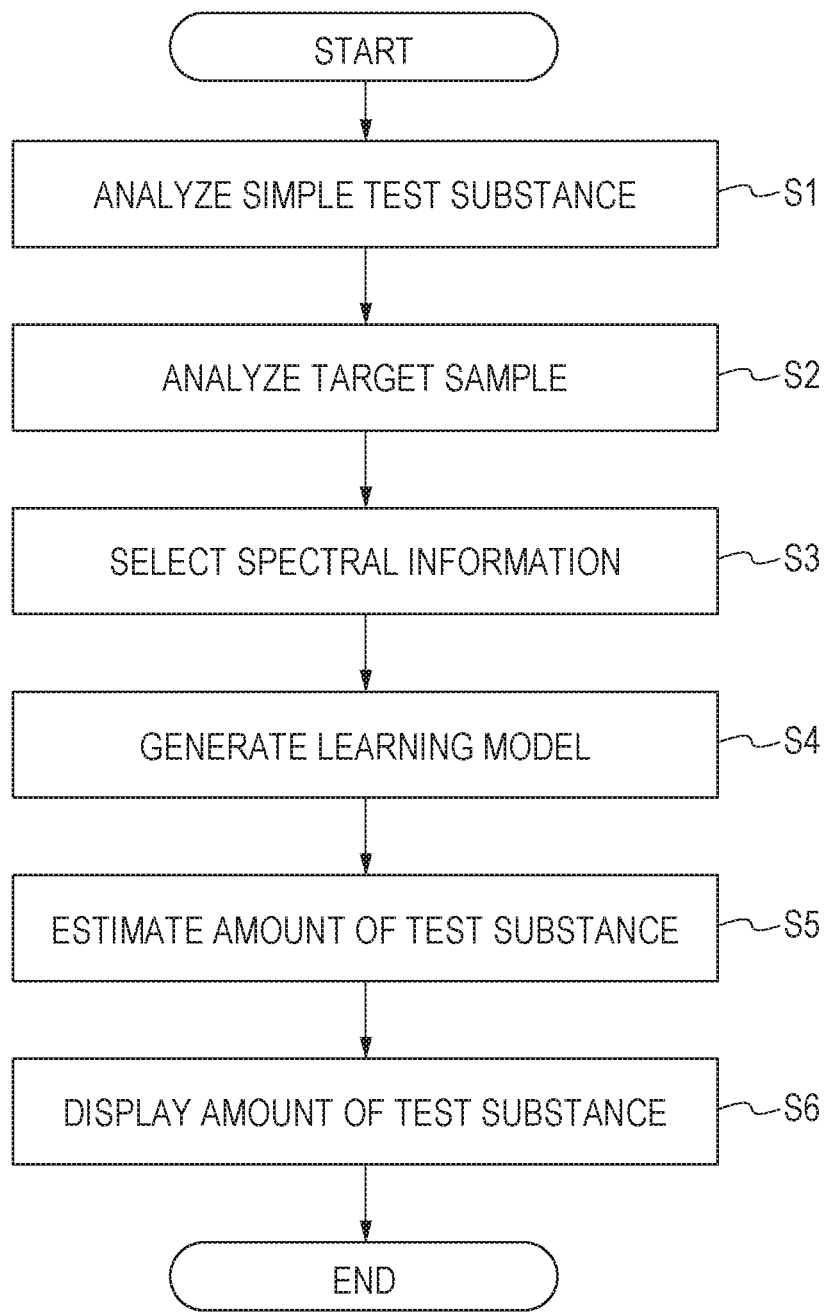
FIG. 2 is a flowchart for processing of calculating the amount of a test substance in a sample according to the embodiment.
Figure 3:
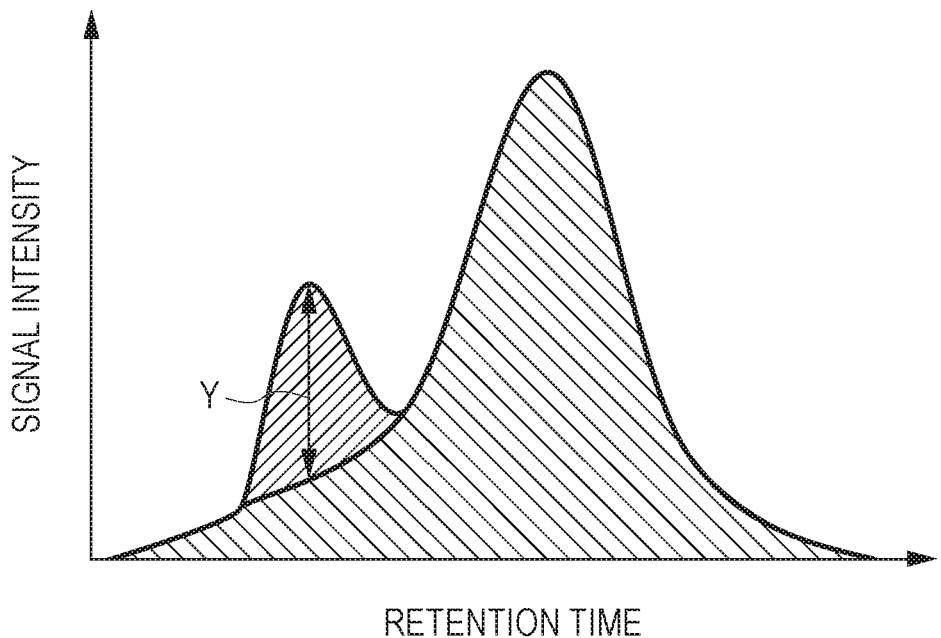
FIG. 3 is a graph illustrating a known peak separation method using a base line.
Figure 4:
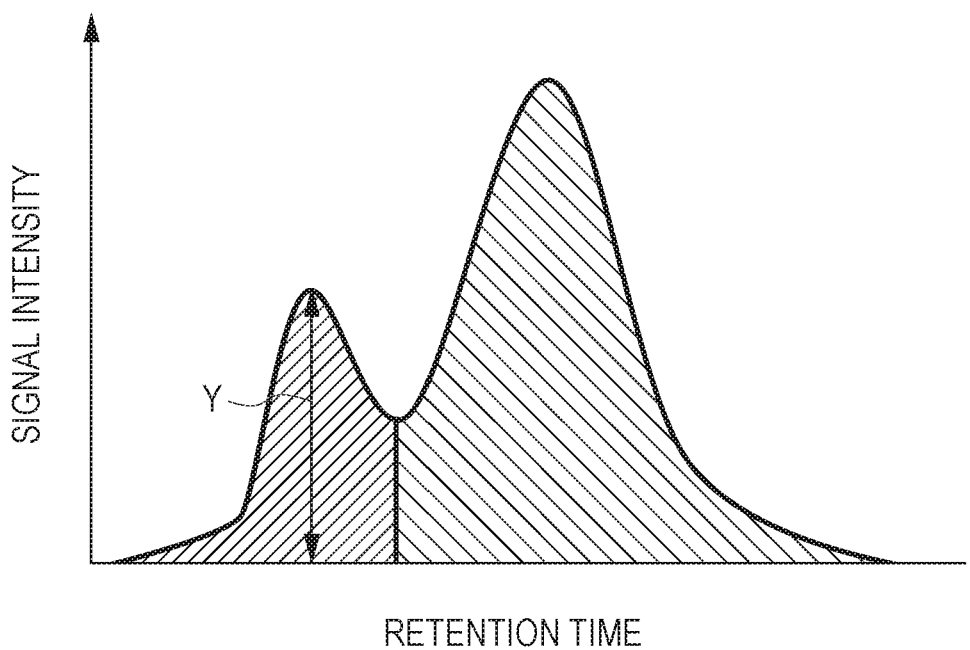
FIG. 4 is a graph illustrating a known vertical peak separation method using a minimum value between peaks.

Referring to FIG. 2, the processing procedure of the present embodiment will be described. FIG. 2 is a flowchart for processing of calculating the amount of the test substance in the sample.

S1: Analyzing Simple Test Substance

First, the analyzing apparatus 23 analyzes a simple test substance (step S1). Analysis conditions may be appropriately selected in the viewpoint of sensitivity, analysis time, and so on. At that time, the concentration of the test substance is changed in several levels. The concentration may be changed in three or more levels, although it depends on the property of the substance. In the case of multiple kinds of test substance, the test substances may be individually analyzed. If the signals of the test substances can be sufficiently separated, the test substances may be measured at the same time. The result of analysis of a simple test substance includes a plurality of pieces of spectral information. The spectral information may include spectral information obtained at different measurement wavelengths.

The analyzing apparatus 23 outputs the acquired spectral information to the information processing apparatus 10. The information processing apparatus 10 receives the spectral information from the analyzing apparatus 23 and stores the spectral information in the RAM 33 or the storage unit 34. The spectral-information acquisition unit 41 acquires the thus-stored spectral information.

As described above, the spectral information, which is the result of analysis, may be stored in the database 22. In this case, the spectral-information acquisition unit 41 acquires the spectral information from the database 22. The timing when the analyzing apparatus 23 analyzes the test substance may be any timing before the selection of the spectral information at step S3.

(S2: Analyzing Target Sample Containing Test Substance and Foreign Substances

The analyzing apparatus 23 analyzes a target sample containing a test substance and foreign substances (step S2). Measurement conditions are set to the same conditions as the conditions at step S1. The result of analysis of the target sample includes a plurality of pieces of spectral information. The spectral information may include spectral information obtained at different measurement wavelengths. The timing when the analyzing apparatus 23 analyzes the target sample may be any timing before the selection of spectral information at step S3.

S3: Selecting Spectral Information

The spectral-information selection unit 47 selects two or more pieces of spectral information from the plurality of pieces of spectral information included in the result of analysis of the simple test substance obtained at step S1 and the plurality of pieces of spectral information included in the result of analysis of the target sample obtained at step S2. The spectral-information acquisition unit 41 acquires connected spectral information on the simple test substance in which the selected pieces of spectral information on the simple test substance are connected and connected spectral information on the target sample in which the selected pieces of spectral information on the target sample are connected.

S4: Generating Learning Model

Subsequently, the learning-model generation unit 42 generates a plurality of pieces of training data using the connected spectral information on the simple test substance obtained at step S3.

A method for generating the training data will be specifically described. The training data is generated by adding any waveforms generated in random numbers to the connected spectral information on the simple test substance. For example, in liquid chromatography, waveforms indicated by spectral information (a chromatogram) often have a Gaussian distribution. For that reason, the learning-model generation unit 42 adds up a plurality of Gaussian curves in which the height of the peak, the median, and the standard deviation are determined in random numbers to generate a plurality of random noises.

The spectral information does not need to be prepared over the entire retention time (the time required until one compound is detected by a detector after injection of the sample. Data on the test substance trimmed, with the peak centered is to be prepared. The accuracy in determining the quantity with the calculation unit, described below, increases as the trimmed range increases. However, this increases the number of training data necessary for increasing the accuracy. In one embodiment, the trimmed range is six times or more and 30 times or less of the standard deviation (a) of the peak of the test substance; ten times or more and 20 times or less; and 14 times or more and 18 times or less.1

Next, any waveforms are added to the trimmed data. In one embodiment, the number of waveforms to be added is a number that may cause the peaks not to be separated to overlap on the chromatogram; or two or more and eight or less. If the number of added waveforms exceeds eight, shape prediction of the peak of the test substance becomes difficult, causing a decrease in quantitative determination accuracy. If the number of added waveforms is less than two, accurate quantitative determination may not be performed on a chromatogram having overlapping peaks. In another embodiment, the number of added waveforms is more three or more and six or less; or four or more and five or less. The shapes of any waveforms are expressed as a Gaussian function in Exp. 1.

$$a \exp\left\{-\frac{(x-b)^2}{2c^2}\right\} \qquad \text{Exp. 1}$$

where a is a value from 0 to α % relative to the assumed peak height of the test substance, and b is a random number in the range of β % of the trimmed range. For example, if the range of ±8σ from the peak center of the test substance is trimmed, b is any value in the range from −8σ×β % to +8σ×β %. In one embodiment the values α and β are 50 or greater and 300 or less; 50 or greater and 250 or less or 50 or greater and 200 or less. The value c is a random number in the range of 0.1 times or greater and 10 times or less of the standard deviation of the peak of the test substance; 0.2 times or more and 8 times or lessor 0.5 times or greater and 5 times or less.

The learning-model generation unit 42 generates a plurality of waveforms in which each of the plurality of random noises and the waveform indicated by the connected spectral information on the test substance are added up. The generated plurality of waveforms are used as spectral information (learning spectral information) on a virtual sample containing a test substance and foreign substances. In other words, the generated plurality of pieces of learning spectral information is determined as input data constituting training data.

Furthermore, the learning-model generation unit 42 determines the height of a peak (quantitative information) specified from the spectral information on the test substance, which is the source of the generated learning spectral information, to be correct data constituting the training data. Thus, the learning-model generation unit 42 generates a plurality of pieces of training data each of which is a set of input data and correct data. In other words, the learning spectral information generated from the spectral information on the selected simple test substance and the quantitative information specified from the selected spectral information on the simple test substance are associated with each other. Since spectral information according to the concentration of the test substance has been obtained at step S1, the learning-model generation unit 42 generates a plurality of pieces of training data for each concentration. The learning-model generation unit 42 may increase the width of the waveform of the chromatogram based on the fact that the peak width tends to increase as the retention time increases.

Japanese Patent Laid-Open No. 2018-152000 discloses a method of machine learning by linking mass spectrum data on the sample to the presence or absence of cancer. However, a large amount of training data is required to increase the accuracy of machine learning. In Japanese Patent Laid-Open No. 2018-152000, 90,000 kinds of data are prepared as training data. In other words, machine learning can accurately analyze complex analysis results but has the disadvantage of requiring a large amount of training data. The present embodiment does not need to prepare a large amount of training data, which is a disadvantage of machine learning, so that the burden on the user can be reduced.

Training data is generated in this way. Alternatively, training data may be generated by analyzing a plurality of samples with the analyzing apparatus 23 to obtain learning spectral information on the samples and combining the spectral information with quantitative information on the test substance. In another alternative, spectral information on a vertical sample may be generated using a method different from the above method.

A learning model is constructed by performing machine learning according to a predetermined algorithm using the generated training data (step S4). Examples of a specific learning method include a method using a neural network and a method using a support vector machine, which are general machine learning methods. Another example is a deep learning method using multiple hidden layers, such as a deep neural network (DNN) and a convolutional neural network (CNN). In the case of multiple kinds of test substance, a learning model is generated for each substance.

S5: Estimating Amount of Test Substance

Subsequently, the estimation unit 44 estimates the amount of the test substance by applying the learning model generated at step S4 to the connected spectral information on the target sample obtained at step S3. At that time, the amount is transformed to the display format of the display unit 36. The display format of the display unit 36 may be concentration, such as g/L and mol/L, or a percentage to the standard amount.

S6: Displaying Amount of Test Substance

Next, the display unit 36 displays the amount of the test substance estimated at step S5 to present the amount to the user (step S6). At that time, the amount may be displayed in a graph format or a table format.

The aspect of the embodiments can also be implemented by supplying a program for implementing one or more functions of the above embodiments to a system or an apparatus via a network or a storage medium and by reading and executing the program with one or more processors of the computer of the system or the apparatus. The aspect of the embodiments can also be implemented by a circuit (for example, an application specific integrated circuit (ASIC)) for performing the functions of one or more of the above embodiments.

EXAMPLES

The present invention will be described in more detail hereinbelow using examples and comparative examples. The aspect of the embodiments is not limited to the examples described below.

Example 1

The following is an example in which the above data processing method is applied to quantitative determination of vanillyl mandelic acid (VMa) in a mixture of VMa and creatinine (Cre) to evaluate the effect of the method. The vertical axis of a chromatogram obtained by high-performance liquid chromatography (HPLC) indicates signal intensity (arbitrary unit (a.u.)), and the horizontal axis indicates time (second). The time required to detect a compound with a detector from injection of a sample is referred to as "retention time".

Checking Retention Time

Figure 5:
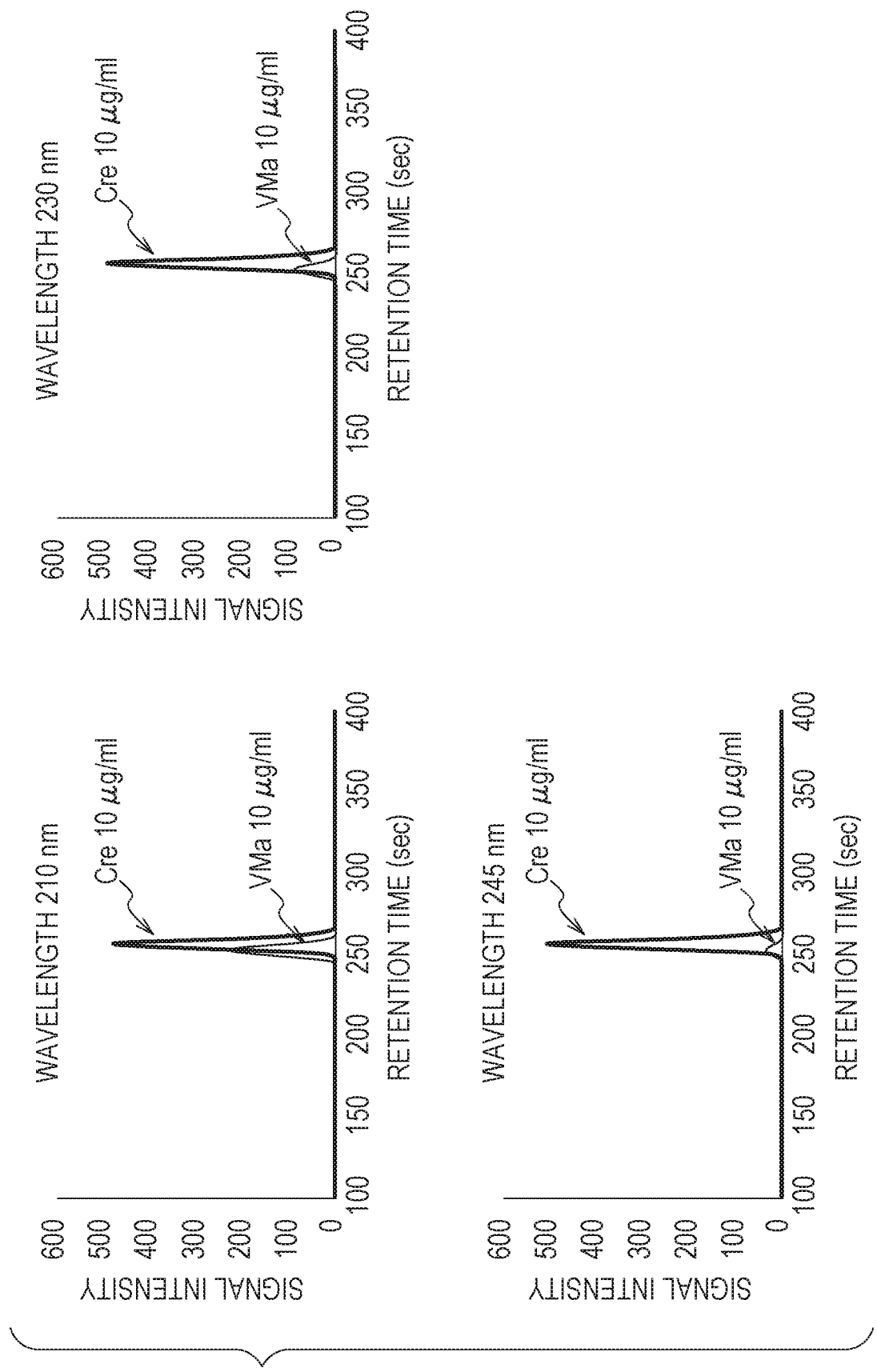
FIG. 5 illustrates chromatograms of a mixture of vanillyl mandelic acid (VMa) and simple creatinine (Cre) at three waveforms (210 nm, 230 nm, and 245 nm).
Figure 6A:
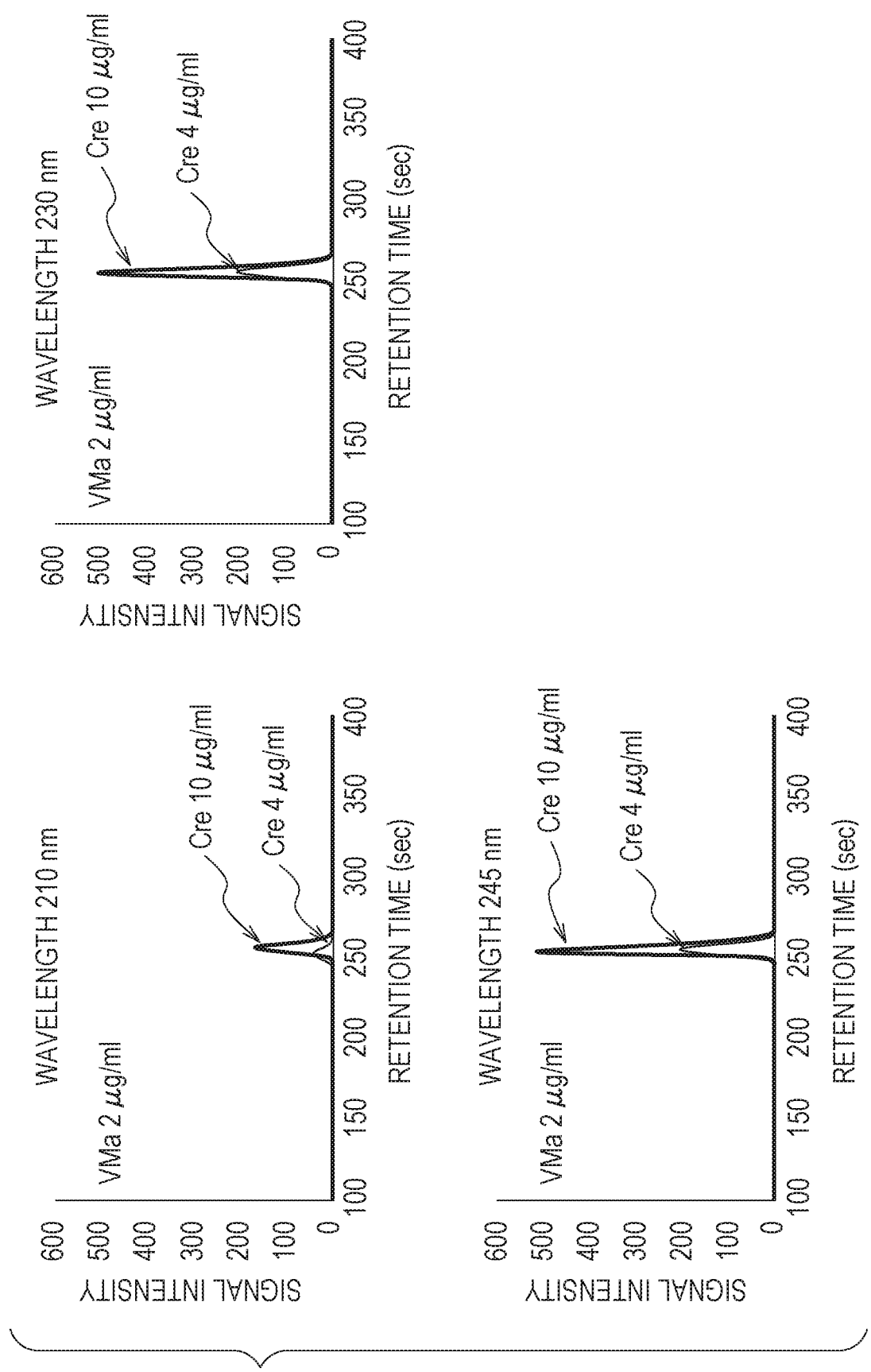
FIGS. 6A to 6E are diagrams of chromatograms of mixtures of VMa with different concentrations and Cre with different concentrations measured at three wavelengths (210 nm, 230 nm, and 245 nm).
Figure 6B:
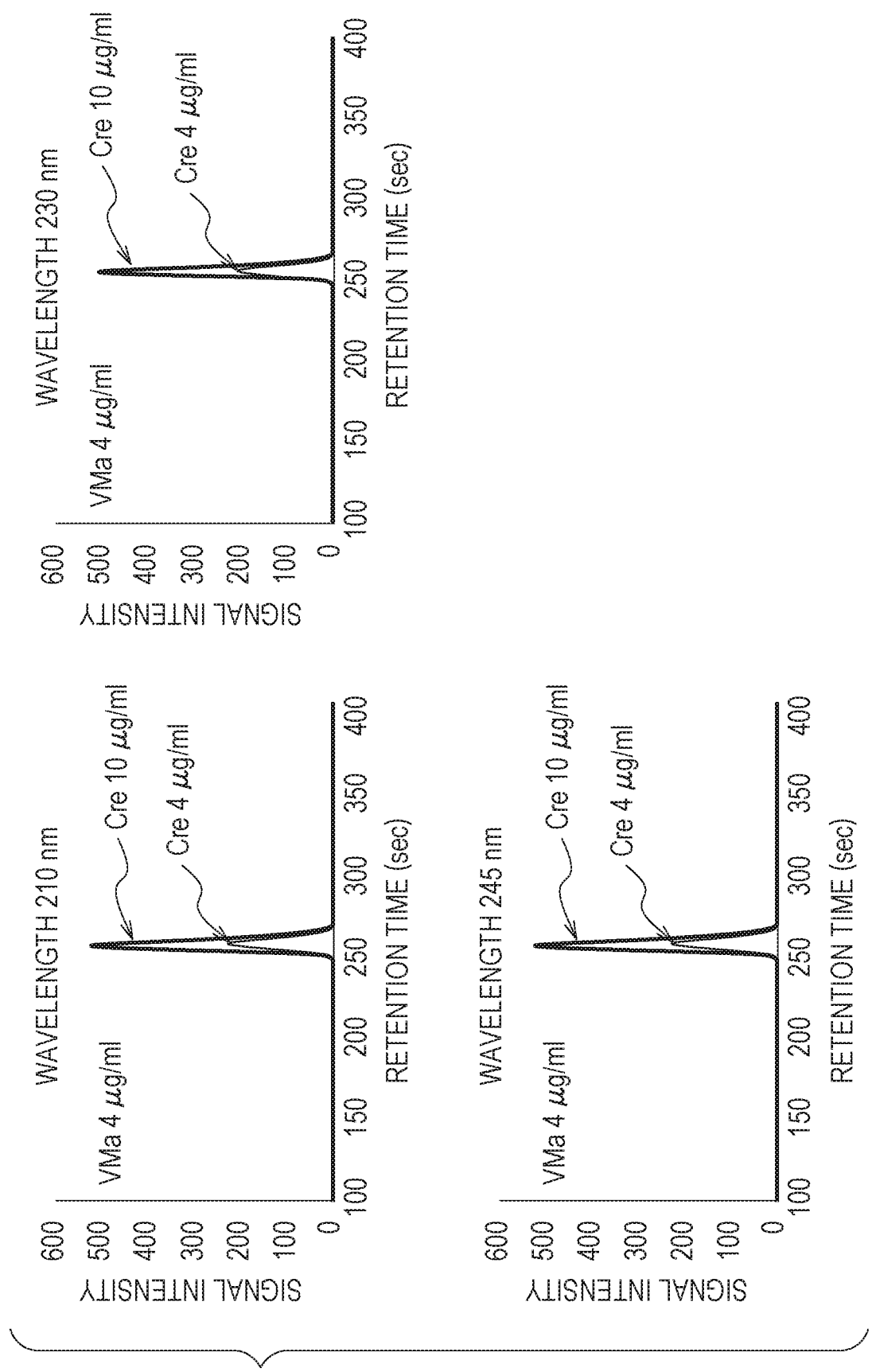
Figure 6C:
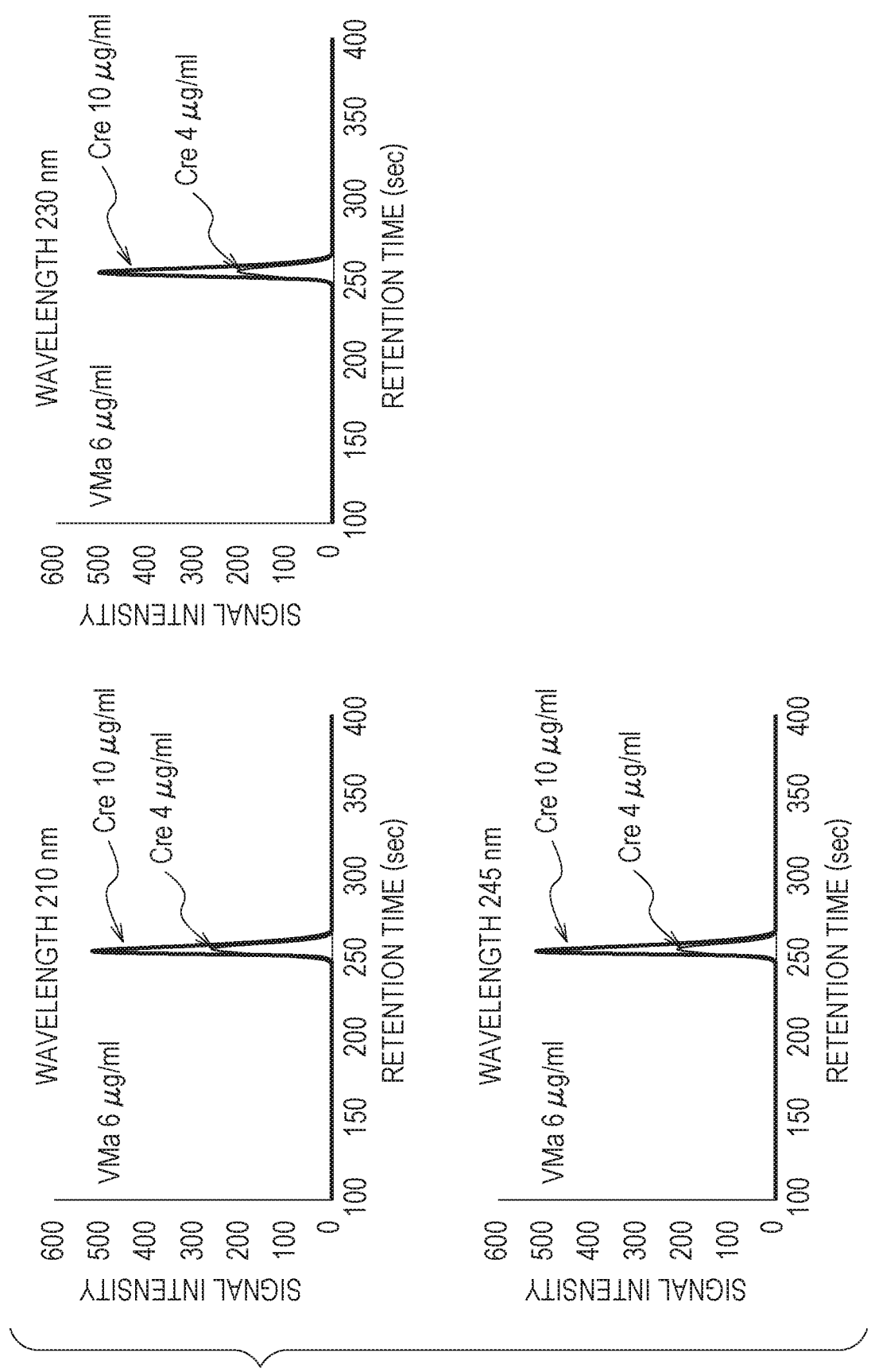
Figure 6D:
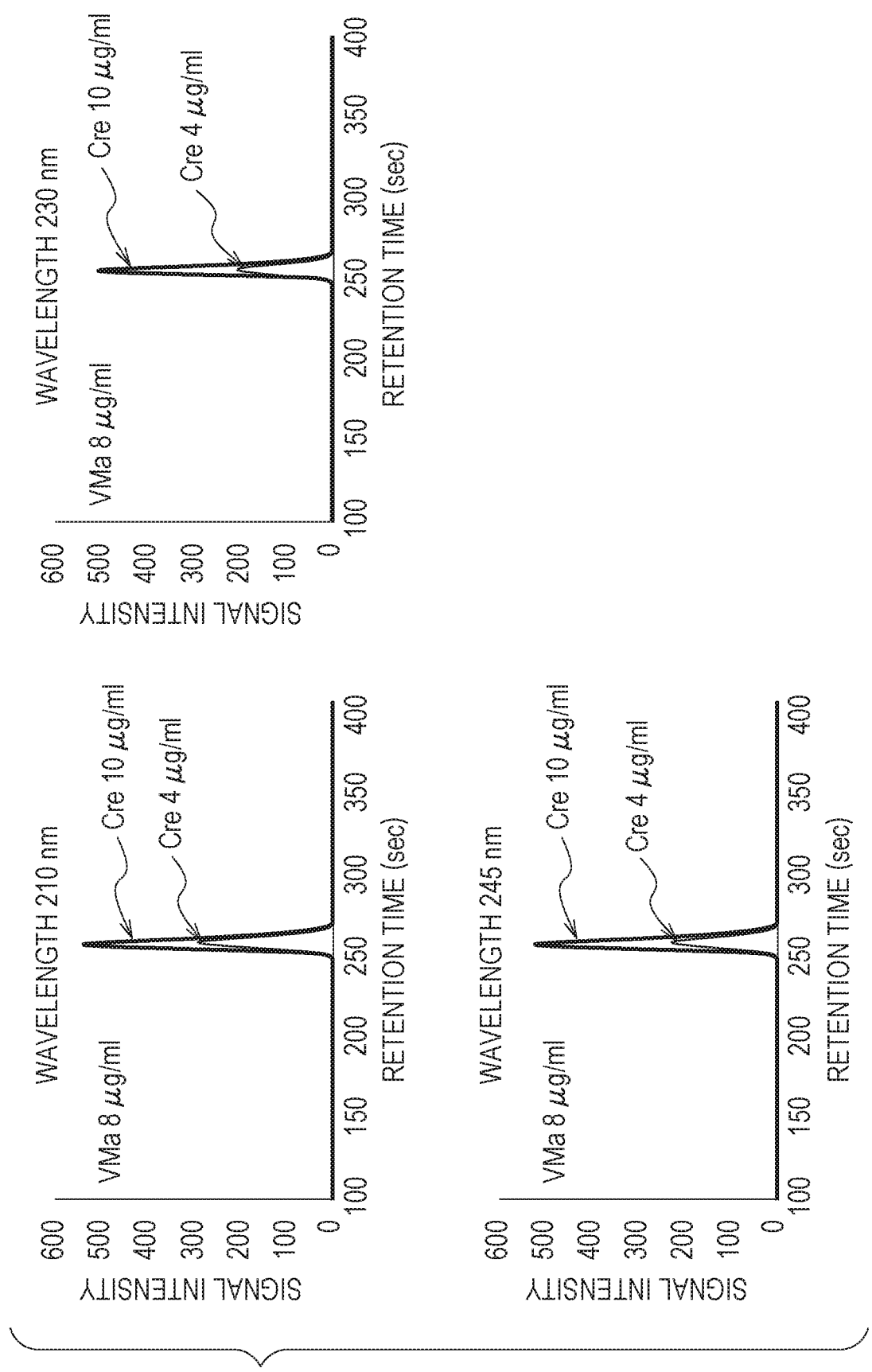
Figure 6E:
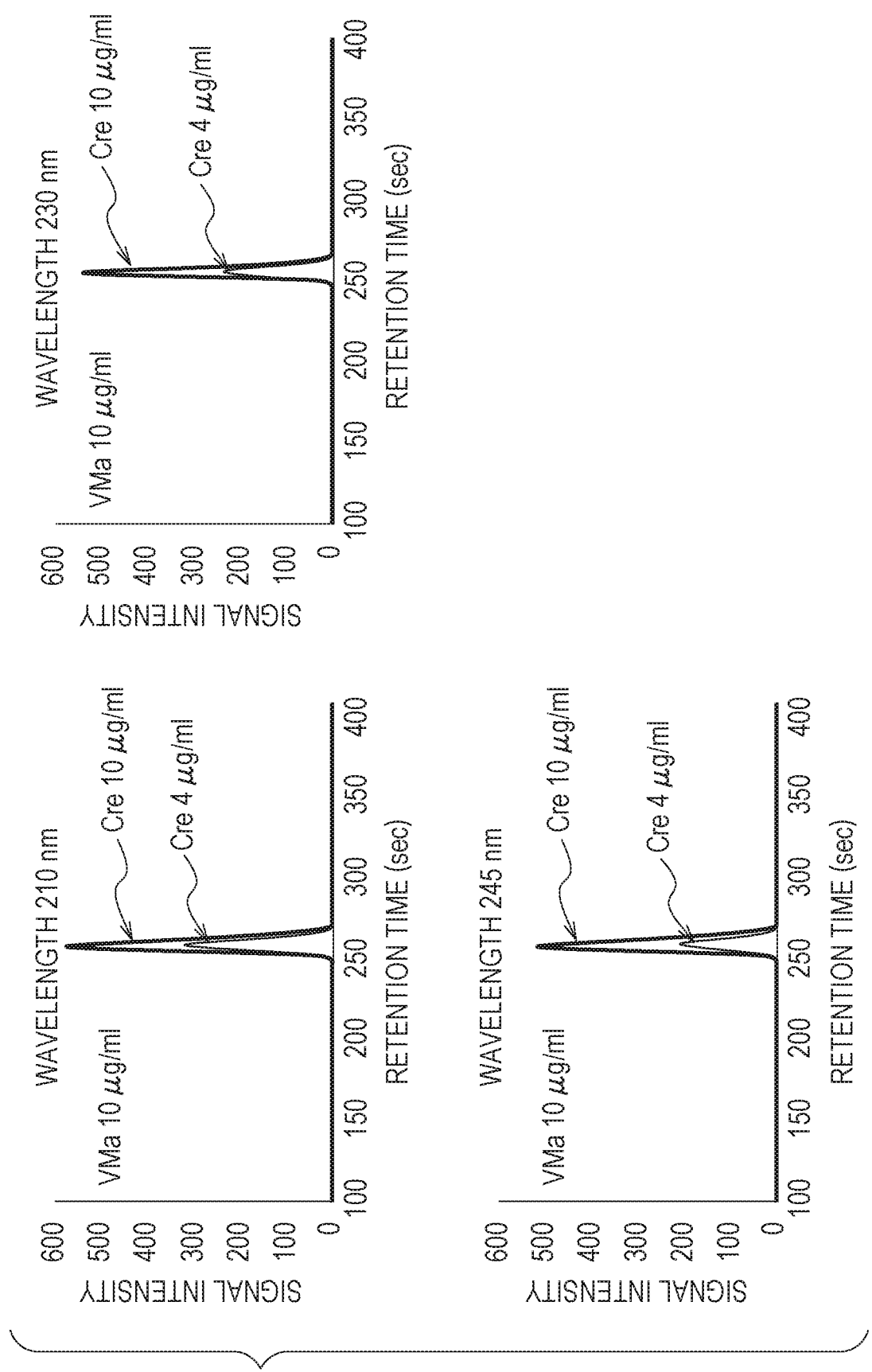
Figure 7A:
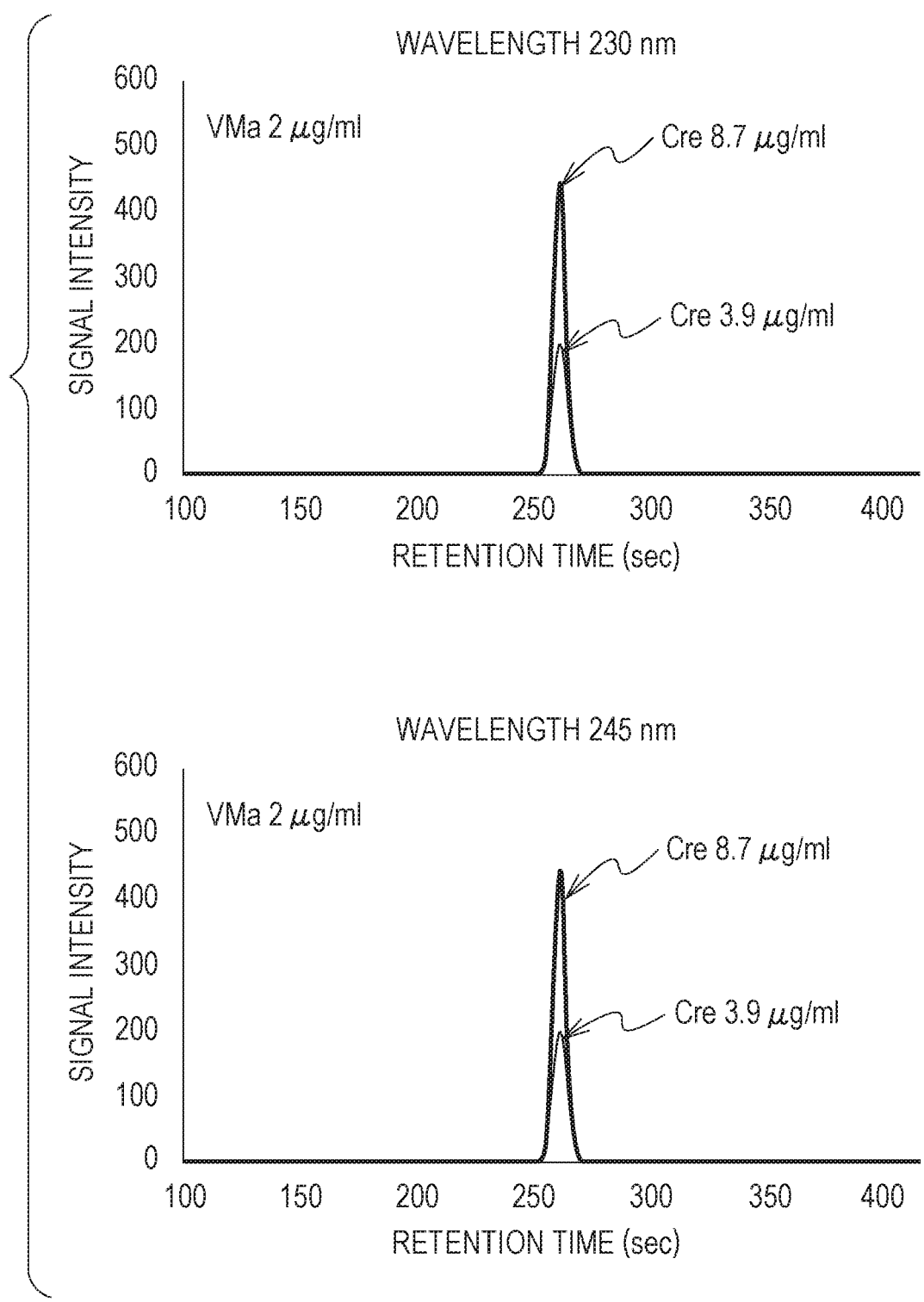
FIGS. 7A to 7E are diagrams of chromatograms of mixtures of VMa with different concentrations and Cre with different concentrations measured at two wavelengths (230 nm and 245 nm).
Figure 7B:
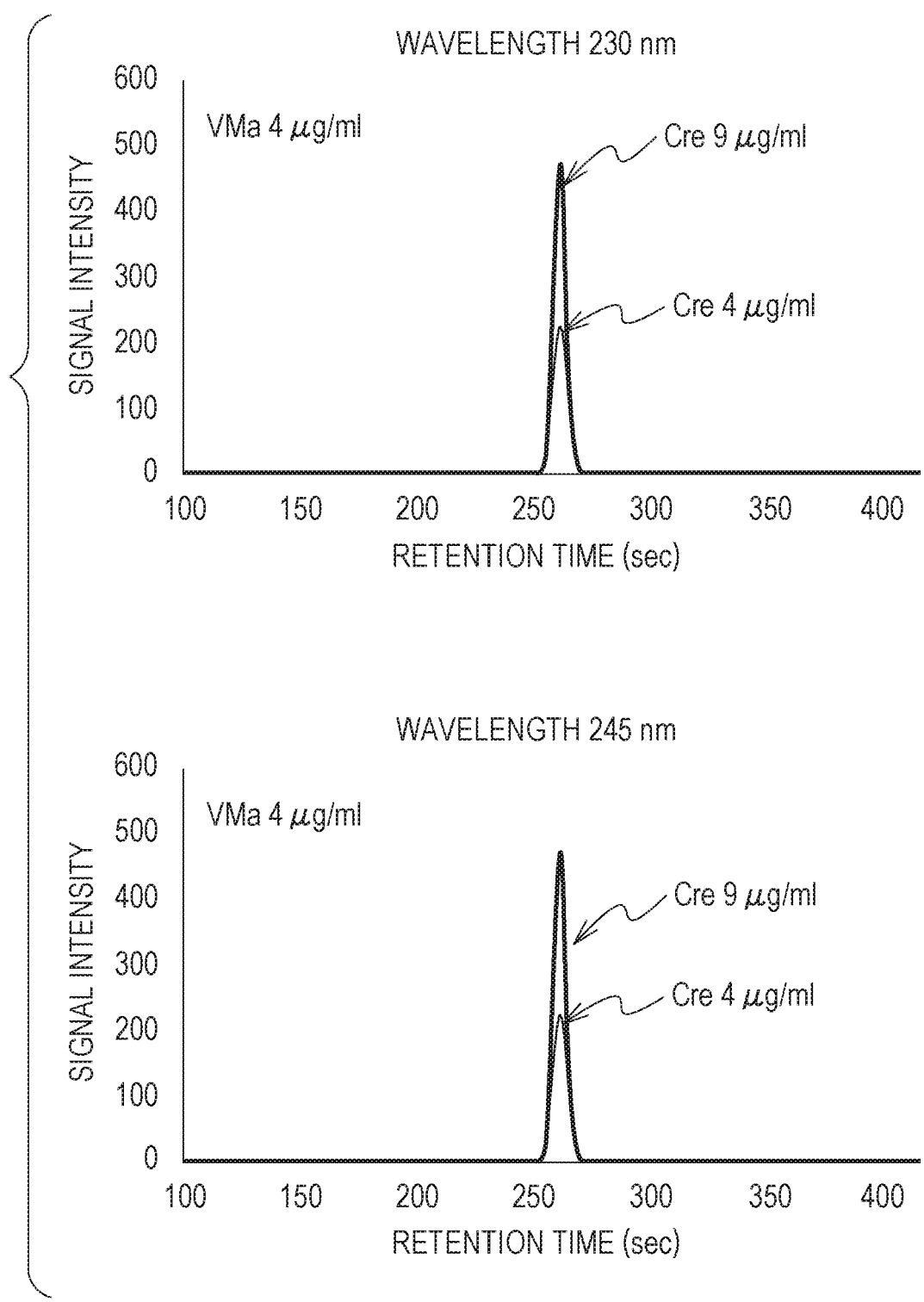
Figure 7C:
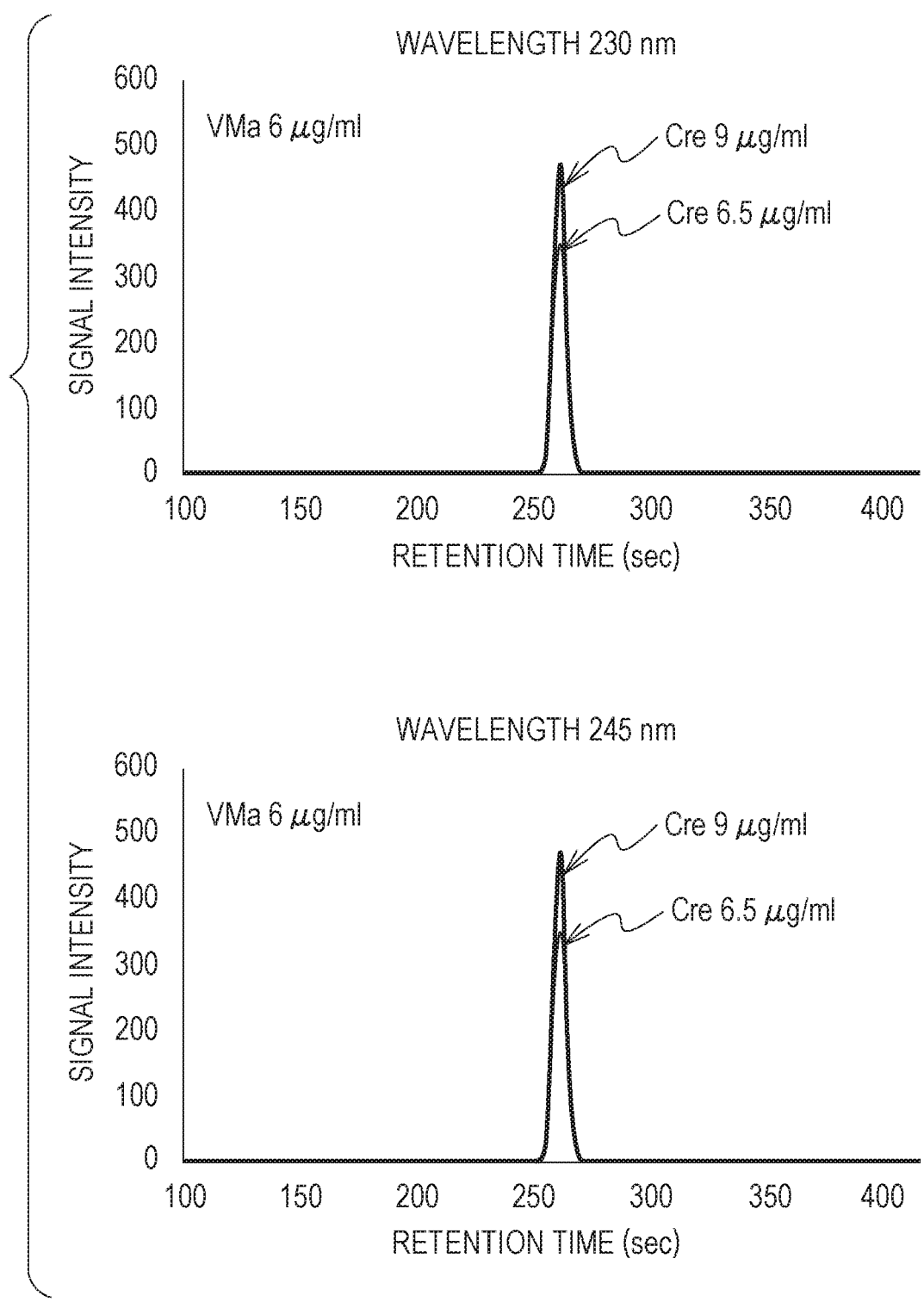
Figure 7D:
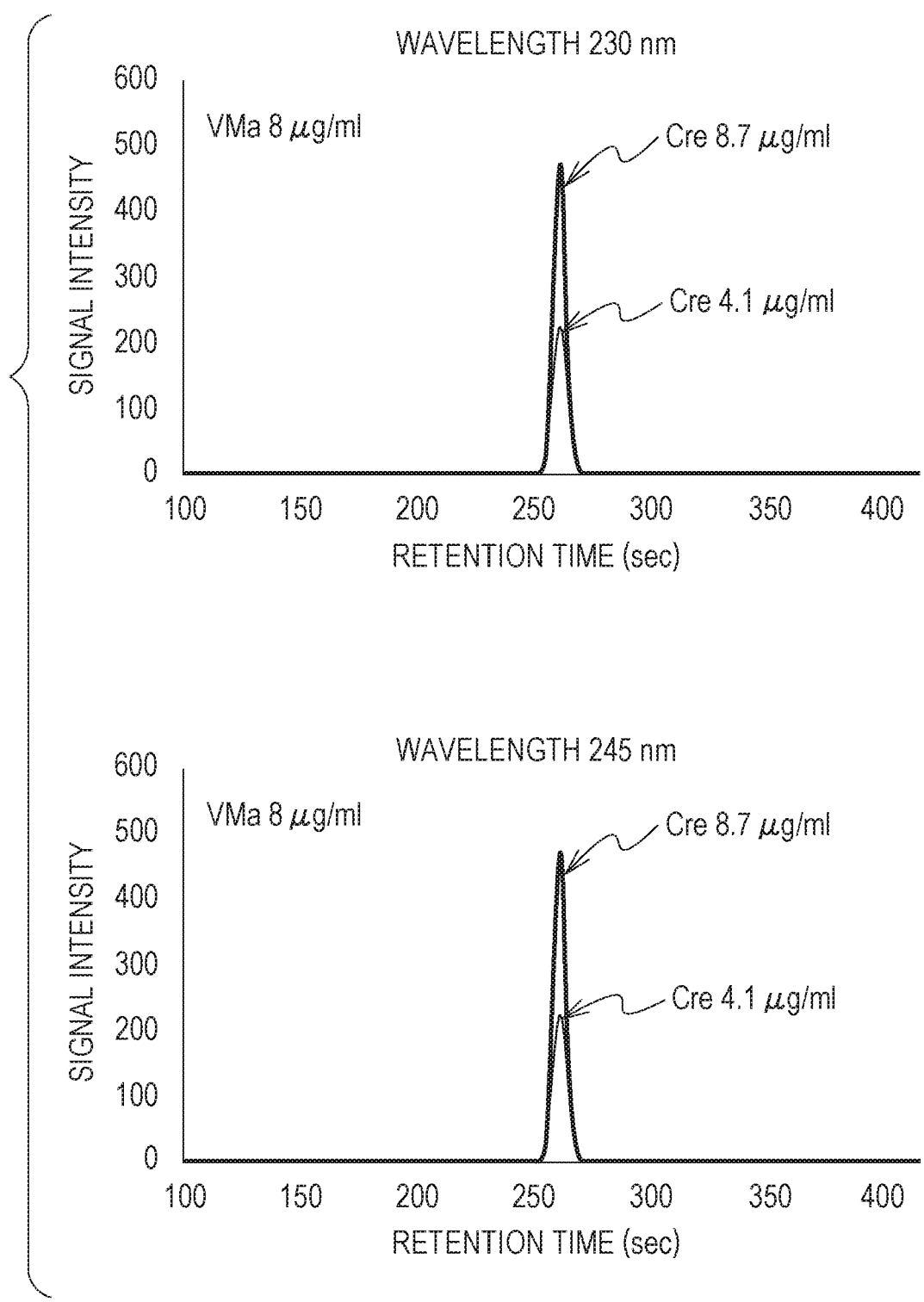
Figure 7E:
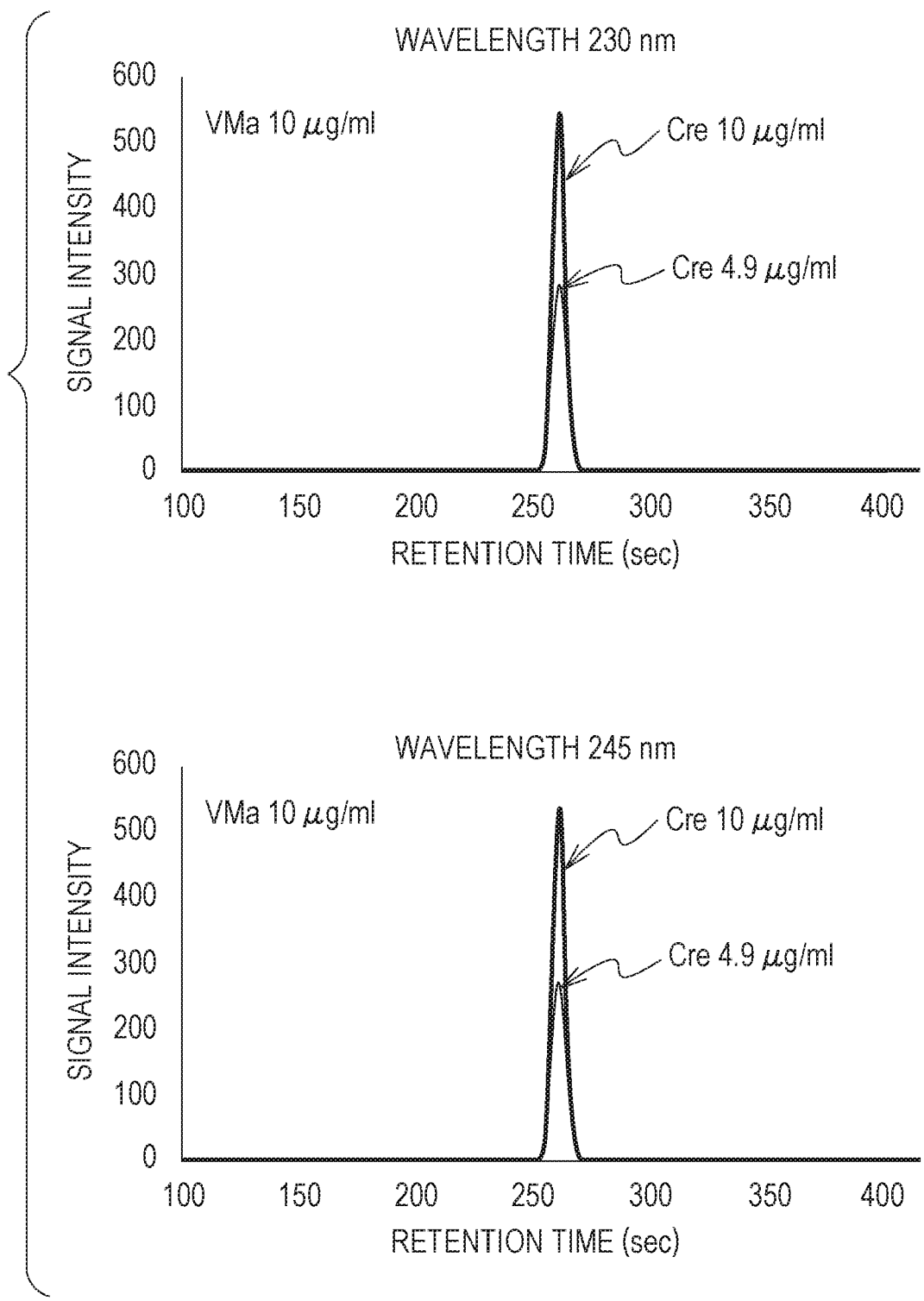

First, VMa (10 µg/ml) and Cre (10 µg/ml) were analyzed by HPLC to obtain chromatograms at three wavelengths (210 nm, 230 nm, and 245 nm) (see FIG. 5). FIG. 5 shows that the retention times of VMa and Cre are substantially the same.

Creating Training Data

Next, training data was created. Chromatograms of each of mixtures of VMa with different concentrations (0.00 µg/ml, 2.00 µg/ml, 4.00 µg/ml, 6.00 µg/ml, 8.00 µg/ml, and 10.00 µg/ml) and Cre measured at three wavelengths (210 nm, 230 nm, and 245 nm) were prepared. At that time, the concentration of Cre was randomly selected in the range of 10 µg/ml or less. The chromatograms measured for each mixture at the three wavelengths were combined to create a simulation chromatogram. This will be described in detail with reference to FIGS. 8A and 8B and FIG. 9.

Figure 8A:
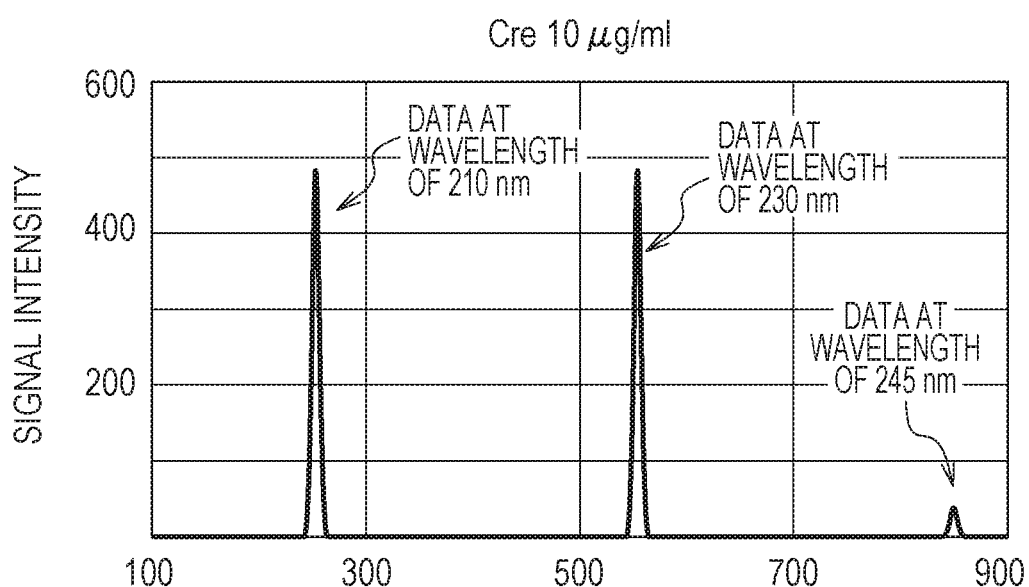
FIG. 8A is a diagram of a simulation chromatogram created by combining the chromatograms of simple Cre measured at three wavelengths.
Figure 8B:
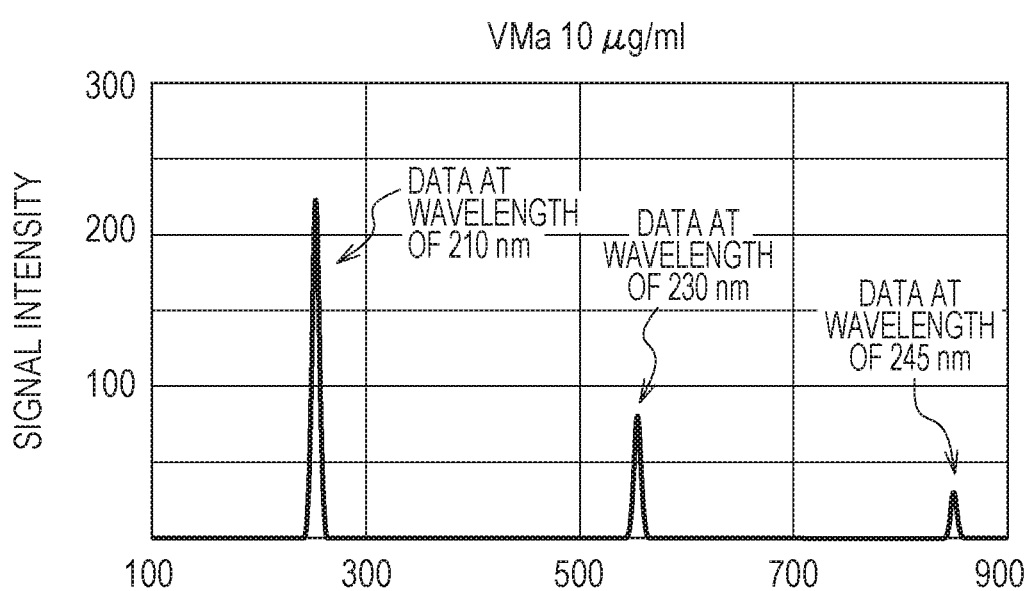
FIG. 8B is a diagram of a simulation chromatogram created by combining the chromatograms of simple VMa measured at three wavelengths.
Figure 9:
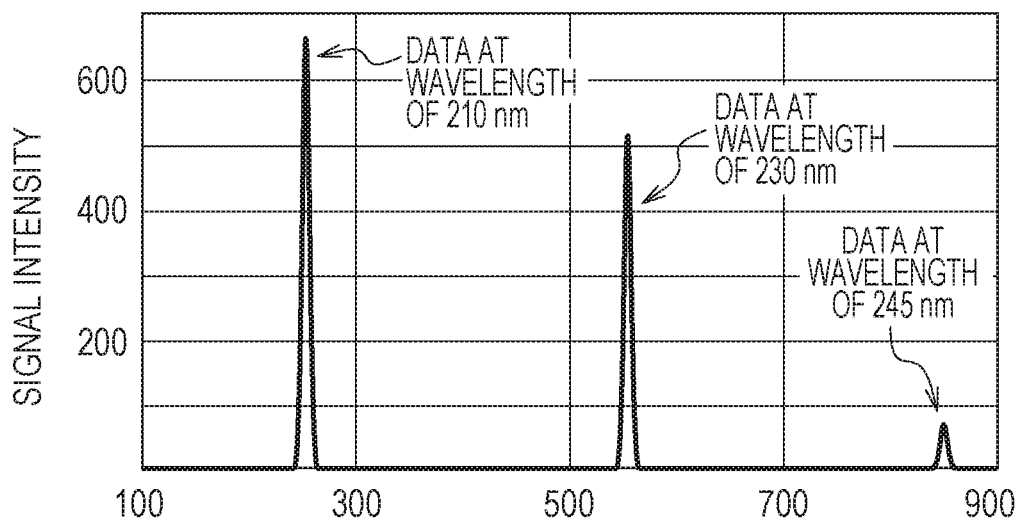
FIG. 9 is a diagram of a simulation chromatogram of a mixture of VMa and Cre.

FIG. 8A is a diagram of a simulation chromatogram created by combining the chromatograms of a 10.00 µg/ml of simple Cre measured at three wavelengths. FIG. 8B is a diagram of a simulation chromatogram created by combining the chromatograms of a 10.00 µg/ml of simple VMa measured at three wavelengths. FIG. 9 is a diagram of a simulation chromatogram of a mixture of the 10.00 µg/ml of VMa and the 10.00 µg/ml of Cre, created from the two simulation chromatograms in FIGS. 8A and 8B.

Four normal distribution waveforms in which the median, the standard deviation, and the peak height are set in random numbers were added to these simulation chromatograms to create sample data. Thousand kinds of sample data were prepared for one data on a specific concentration of VMa. Each sample data and the peak height of VMa contained in the sample data were combined to create 5,000 pieces of training data.

Generating Learning Model

A learning model was generated by performing machine learning based on the created training data. For the machine learning, a fully connected neural network was used, and a ReLU function and a linear function were used as activation functions. A mean square error was used as a loss function, and Adam was used for an optimization algorithm. To obtain sufficient determination accuracy, repeat operation of about 100 epochs was performed.

Checking Accuracy Using Learning Model

Chromatograms of mixtures of VMa with different concentrations (2.00 µg/ml, 4.00 µg/ml, 6.00 µg/ml, 8.00 µg/ml, and 10.00 µg/ml) and Cre with different concentrations (4.00 µg/ml and 10.00 µg/ml) measured at three wavelengths (210 nm, 230 nm, and 245 nm) were prepared (see FIGS. 6A to 6E). The chromatograms measured at the three wavelengths for each mixture were connected to create a simulation chromatogram.

Each simulation chromatogram was applied to the generated learning model to estimate a peak height corresponding to VMa. Table 1 describes the estimation results and the correlation coefficient. This shows that the value of the correlation coefficient $R^2$ between the charge amount of VMa and the estimated value of VMa is as great as 0.674, so that quantitative information on VMa can be estimated with high accuracy.

TABLE 1

| Sample No. | Charge amount of VMa (µg/ml) | Charge amount of Cre (µg/ml) | Estimated value of VMa (µg/ml) | Correlation coefficient $R^2$ |
|---|---|---|---|---|
| 1-1 | 2.00 | 4.00 | 5.22 | 0.674 |
| 1-2 | 2.00 | 10.00 | 9.05 | |
| 1-3 | 4.00 | 4.00 | 7.38 | |
| 1-4 | 4.00 | 10.00 | 11.39 | |
| 1-5 | 6.00 | 4.00 | 9.2 | |
| 1-6 | 6.00 | 10.00 | 13.34 | |
| 1-7 | 8.00 | 4.00 | 11.21 | |
| 1-8 | 8.00 | 10.00 | 14.92 | |
| 1-9 | 10.00 | 4.00 | 13.32 | |
| 1-10 | 10.00 | 10.00 | 17.34 | |

Example 2

The accuracy was checked using a learning model in the same manner as in EXAMPLE 1 except that the measurement wavelengths for the chromatogram were changed from three kinds to two kinds (230 nm and 245 nm). Each simulation chromatogram was applied to the generated learning model to estimate a peak height corresponding to VMa. Table 2 describes the estimation results and the correlation coefficient. This shows that the value of the correlation coefficient $R^2$ between the charge amount of VMa and the estimated value of VMa is as great as 0.634, so that the quantitative information on VMa could be estimated with high accuracy.

TABLE 2

| Sample No. | Charge amount of VMa (µg/ml) | Charge amount of Cre (µg/ml) | Estimated value of VMa (µg/ml) | Correlation coefficient $R^2$ |
|---|---|---|---|---|
| 2-1 | 2.00 | 4.00 | 3.56 | 0.634 |
| 2-2 | 2.00 | 10.00 | 0.39 | |
| 2-3 | 4.00 | 4.00 | 0.64 | |
| 2-4 | 4.00 | 10.00 | 1.48 | |
| 2-5 | 6.00 | 4.00 | 4.32 | |
| 2-6 | 6.00 | 10.00 | 5.07 | |
| 2-7 | 8.00 | 4.00 | 10.38 | |
| 2-8 | 8.00 | 10.00 | 10.04 | |
| 2-9 | 10.00 | 4.00 | 7.53 | |
| 2-10 | 10.00 | 10.00 | 6.68 | |

Comparative Example 1

The accuracy was checked using a learning model in the same manner as in EXAMPLE 1 except that the measurement wavelengths for the chromatogram were changed from three kinds to one kind (230 nm). Each simulation chromatogram was applied to the generated learning model to estimate a peak height corresponding to VMa. Table 3 describes the estimation results and the correlation coefficient. This shows that the value of the correlation coefficient $R^2$ between the charge amount of VMa and the estimated value of VMa is as small as 0.069, so that the quantitative information on VMa could not be estimated with high accuracy.

TABLE 3

| Sample No. | Charge amount of VMa (µg/ml) | Charge amount of Cre (µg/ml) | Estimated value of VMa (µg/ml) | Correlation coefficient $R^2$ |
|---|---|---|---|---|
| 3-1 | 2.00 | 4.00 | 1.59 | 0.069 |
| 3-2 | 2.00 | 10.00 | 7.84 | |
| 3-3 | 4.00 | 4.00 | 6.35 | |
| 3-4 | 4.00 | 10.00 | 2.29 | |
| 3-5 | 6.00 | 4.00 | 5.52 | |
| 3-6 | 6.00 | 10.00 | 3.76 | |
| 3-7 | 8.00 | 4.00 | 5.88 | |
| 3-8 | 8.00 | 10.00 | 2.76 | |
| 3-9 | 10.00 | 4.00 | 6.19 | |
| 3-10 | 10.00 | 10.00 | 7.03 | |

Comparative Example 2

The accuracy was checked using a learning model in the same manner as in EXAMPLE 1 except that the measurement wavelengths for the chromatogram were changed from three kinds to one kind (245 nm). Each simulation chromatogram was applied to the generated learning model to estimate a peak height corresponding to VMa. Table 4 describes the estimation results and the correlation coefficient. This shows that the value of the correlation coefficient $R^2$ between the charge amount of VMa and the estimated value of VMa is as small as 0.035, so that the quantitative information on VMa could not be estimated with high accuracy.

TABLE 4

| Sample No. | Charge amount of VMa (µg/ml) | Charge amount of Cre (µg/ml) | Estimated value of VMa (µg/ml) | Correlation coefficient $R^2$ |
|---|---|---|---|---|
| 2-1 | 2.00 | 4.00 | 5.44 | 0.035 |
| 2-2 | 2.00 | 10.00 | 6.29 | |
| 2-3 | 4.00 | 4.00 | 2.95 | |
| 2-4 | 4.00 | 10.00 | 4.25 | |
| 2-5 | 6.00 | 4.00 | 4.41 | |
| 2-6 | 6.00 | 10.00 | 7.17 | |
| 2-7 | 8.00 | 4.00 | 6.65 | |
| 2-8 | 8.00 | 10.00 | 6.66 | |
| 2-9 | 10.00 | 4.00 | 1.78 | |
| 2-10 | 10.00 | 10.00 | 4.70 | |

Example 3

The following is an example in which the above data processing method is applied to quantitative determination of both of VMa and Cre to evaluate the effect of the method.
Creating Training Data
Training data was created. Chromatograms of each of mixtures of VMa with different concentrations (0.00 µg/ml, 2.00 µg/ml, 4.00 µg/ml, 6.00 µg/ml, 8.00 µg/ml, and 10.00 µg/ml) and Cre measured at two wavelengths (230 nm and 245 nm) were prepared. At that time, the concentration of Cre was randomly selected in the range of 10 µg/ml or less. The chromatograms measured for each mixture at the two wavelengths were combined to create a simulation chromatogram.

Four normal distribution waveforms in which the median, the standard deviation, and the peak height are set in random numbers were added to these simulation chromatograms to create sample data. Thousand kinds of sample data were prepared for one data on a specific concentration of VMa. Each sample data and the peak heights of VMa and Cre contained in the sample data were combined to create 5,000 pieces of training data.
Generating Learning Model
A learning model was generated by performing machine learning based on the created training data. For the machine learning, a fully connected neural network was used, and a ReLU function and a linear function were used as activation functions. A mean square error was used as a loss function, and Adam was used for an optimization algorithm. To obtain sufficient determination accuracy, repeat operation of about 100 epochs was performed.
Checking Accuracy Using Learning Model
Chromatograms of mixtures of VMa with different concentrations (2.00 µg/ml, 4.00 µg/ml, 6.00 µg/ml, 8.00 µg/ml, and 10.00 µg/ml) and Cre with different concentrations (about 4.00 µg/ml and about 10.00 µg/ml) measured at two wavelengths (230 nm and 245 nm) were prepared (see FIGS. 7A to 7E). The chromatograms measured at the two wavelengths for each mixture were connected to create a simulation chromatogram.

Each simulation chromatogram was applied to the generated learning model to estimate peak heights corresponding to VMa and Cre. Table 5 describes the estimation results and the correlation coefficients. This shows that the value of the correlation coefficient $R^2$ between the charge amount of VMa and the estimated value of VMa is as great as 1.000 and that the value of the correlation coefficient $R^2$ between the charge amount of Cre and the estimated value of Cre is as great as 0.975, so that the quantitative information on VMa and Cre could be estimated with high accuracy.

TABLE 5

| Sample No. | Charge amount of VMa (µg/ml) | Charge amount of Cre (µg/ml) | Estimated value of VMa (µg/ml) | Estimated value of Cre (µg/ml) | Correlation coefficient of VMa $R^2$ | Correlation coefficient of Cre $R^2$ |
|---|---|---|---|---|---|---|
| 5-1 | 2.00 | 3.90 | 2.00 | 3.90 | 1.000 | 0.975 |
| 5-2 | 2.00 | 8.70 | 2.10 | 8.60 | | |
| 5-3 | 4.00 | 4.00 | 4.10 | 4.30 | | |
| 5-4 | 4.00 | 9.00 | 4.10 | 9.30 | | |
| 5-5 | 6.00 | 6.50 | 6.00 | 6.70 | | |
| 5-6 | 6.00 | 9.00 | 6.00 | 10.00 | | |
| 5-7 | 8.00 | 4.10 | 8.00 | 5.60 | | |
| 5-8 | 8.00 | 8.70 | 8.10 | 8.50 | | |
| 5-9 | 10.00 | 4.90 | 10.00 | 4.70 | | |
| 5-10 | 10.00 | 10.00 | 10.00 | 10.10 | | |

While the disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-121955, filed Jun. 28, 2019 and No. 2020-076006, filed Apr. 22, 2020, which are hereby incorporated by reference herein in their entirety.

What is claimed is:

1. An apparatus comprising:
a database storing a learning model;
a processor; and
a memory containing instructions that, when executed by the processor, causing the processor to perform operations as:
an analyzing apparatus configured to analyze: (1) a first test substance to produce a plurality of test pieces of test spectral information, and (2) a target sample including a mixture of a second test substance and a foreign substance to produce a plurality of sample pieces of sample spectral information;
a selection unit configured to select two or more test pieces and two or more sample pieces;
an acquisition unit configured to acquire combined test spectral information of the two or more test pieces and combined sample spectral information of the two or more sample pieces;
a generation unit configured to generate a trained learning model using training data from the selected two or more test pieces; and
an estimation unit configured to estimate an amount of the second test substance by applying the trained learning model to the combined sample spectral information,
wherein estimated amount is transformed to a display format of a display unit.

2. The apparatus according to claim 1, wherein the spectral information is selected based on a wavelength used for measuring a spectrum.

3. The apparatus according to claim 1, wherein the selected spectral information is more in number than a kind of the test substance.

4. The apparatus according to claim 1, wherein the spectral information comprises at least one selected from a group consisting of a chromatogram, a photoelectron spectrum, an infrared absorption spectrum, a nuclear magnetic resonance spectrum, a fluorescence spectrum, a fluorescent X-ray spectrum, an ultraviolet-visible absorption spectrum, a Raman spectrum, an atomic absorption spectrum, a frame emission spectrum, an emission spectrum, an X-ray absorption spectrum, an X-ray diffraction spectrum, a paramagnetic resonance absorption spectrum, an electron spin resonance spectrum, and a thermal-analysis spectrum.

5. The apparatus according to claim 1, further comprising:
an analyzing unit configured to analyze the sample to acquire a plurality of pieces of spectral information on the sample.

6. The apparatus according to claim 5, wherein the analyzing unit uses at least one selected from a group consisting of chromatography, capillary electrophoresis, photoelectric spectroscopy, infrared absorption spectroscopy, nuclear magnetic resonance spectroscopy, fluorescent spectroscopy, fluorescent X-ray spectroscopy, visible-ultraviolet absorption spectroscopy, Raman spectroscopy, an atomic absorption method, frame emission spectroscopy, emission spectroscopy, X-ray absorption spectroscopy, an X-ray diffraction method, electron spin resonance spectroscopy, and a thermo-analytical method.

7. The apparatus according to claim 1, wherein the learning model is a learning model learned using, as training data, a plurality of sets of learning spectral information generated based on the selected spectral information and quantitative information on the test substance specified based on the selected spectral information.

8. The apparatus according to claim 7, wherein the learning spectral information is generated using the selected spectral information and a random noise.

9. The apparatus according to claim 8, wherein the random noise comprises a waveform obtained by a combination of a plurality of Gaussian functions.

10. The apparatus according to claim 1, wherein the test substance comprises at least one selected from a group consisting of protein, deoxyribonucleic acid (DNA), virus, fungi, water-soluble vitamins, fat-soluble vitamins, organic acids, fatty acids, amino acids, sugars, agricultural chemicals, and environmental hormones.

11. The apparatus according to claim 10, wherein the test substance comprises organic acids.

12. The apparatus according to claim 11, wherein the organic acids comprise a vanillyl mandelic acid and creatinine.

13. The apparatus according to claim 1, wherein the quantitative information comprises at least one selected from a group consisting of an amount of the test substance in the sample, a concentration of the test substance in the sample, presence or absence of the test substance in the sample, a ratio of the concentration or the amount of the test substance in the sample to a standard amount of the test substance, and a proportion of the concentration or the amount of the test substance in the sample.

14. A method comprising:
analyzing by an analyzing apparatus: (1) a first test substance to produce a plurality of test pieces of test spectral information, and (2) a target sample including a mixture of a second test substance and a foreign substance to produce a plurality of sample pieces of sample spectral information;
selecting two or more test pieces and two or more sample pieces;
acquiring combined test spectral information of the two or more test pieces and combined sample spectral information of the two or more sample pieces;
generating a trained learning model using training data from the selected two or more test pieces; and
estimating an amount of the second test substance by applying the trained learning model to the combined sample spectral information,
wherein estimated amount is transformed to a display format of a display unit.

15. The method according to claim 14, wherein the spectral information is selected based on a wavelength used for measuring a spectrum.

16. The method according to claim 14, wherein the selected spectral information is more in number than a kind of the test substance.

17. The method according to claim 14, wherein the spectral information comprises at least one selected from a group consisting of a chromatogram, a photoelectron spectrum, an infrared absorption spectrum, a nuclear magnetic resonance spectrum, a fluorescence spectrum, a fluorescent X-ray spectrum, an ultraviolet-visible absorption spectrum, a Raman spectrum, an atomic absorption spectrum, a frame emission spectrum, an emission spectrum, an X-ray absorption spectrum, an X-ray diffraction spectrum, a paramagnetic resonance absorption spectrum, an electron spin resonance spectrum, and a thermal-analysis spectrum.

18. The method according to claim 14, further comprising:
analyzing the sample to acquire a plurality of pieces of spectral information on the sample.

19. The method according to claim 18, wherein the analyzing is performed using at least one selected from a group consisting of chromatography, capillary electrophoresis, photoelectric spectroscopy, infrared absorption spectroscopy, nuclear magnetic resonance spectroscopy, fluorescent spectroscopy, fluorescent X-ray spectroscopy, visible-ultraviolet absorption spectroscopy, Raman spectroscopy, an atomic absorption method, frame emission spectroscopy, emission spectroscopy, X-ray absorption spectroscopy, an X-ray diffraction method, electron spin resonance spectroscopy, and a thermo-analytical method.

20. The method according to claim 14, wherein the learning model is a learning model learned using, as training data, a plurality of sets of learning spectral information generated based on the selected spectral information and quantitative information on the test substance specified based on the selected spectral information.

21. The method according to claim 20, wherein the learning spectral information is generated using the selected spectral information and a random noise.

22. The method according to claim 21, wherein the random noise is a waveform obtained by a combination of a plurality of Gaussian functions.

23. The method according to claim 14, wherein the test substance comprises at least one selected from a group consisting of protein, deoxyribonucleic acid (DNA), virus, fungi, water-soluble vitamins, fat-soluble vitamins, organic acids, fatty acids, amino acids, sugars, agricultural chemicals, and environmental hormones.

24. The method according to claim 23, wherein the test substance comprises organic acids.

25. The method according to claim 24, wherein the organic acids comprise a vanillyl mandelic acid and creatinine.

26. The method according to claim 14, wherein the quantitative information comprises at least one selected from a group consisting of an amount of the test substance in the sample, a concentration of the test substance in the sample, presence or absence of the test substance in the sample, a ratio of the concentration or the amount of the test substance in the sample to a standard amount of the test substance, and a proportion of the concentration or the amount of the test substance in the sample.

27. A non-transitory computer-readable recording medium that records a control program for executing a method, the method comprising:
analyzing: (1) a first test substance to produce a plurality of test pieces of test spectral information, and (2) a target sample including a mixture of a second test substance and a foreign substance to produce a plurality of sample pieces of sample spectral information;
selecting two or more test pieces and two or more sample pieces;
acquiring combined test spectral information of the two or more test pieces and combined sample spectral information of the two or more sample pieces;
generating a trained learning model using training data from the selected two or more test pieces; and
estimating an amount of the second test substance by applying the trained learning model to the combined sample spectral information,
wherein estimated amount is transformed to a display format of a display unit.

28. An apparatus comprising:
a database storing a learning model;
a processor; and
a memory containing instructions that, when executed by the processor, causing the processor to perform operations as:
an analyzing apparatus configured to analyze: (1) a first test substance to produce a plurality of test pieces of test spectral information, and (2) a target sample including a mixture of a second test substance and a foreign substance to produce a plurality of sample pieces of sample spectral information;
a selection unit configured to select two or more test pieces and two or more sample pieces;
an acquisition unit configured to acquire combined test spectral information of the two or more test pieces and combined sample spectral information of the two or more sample pieces;
a generation unit configured to generate a trained learning model using training data from the selected two or more test pieces; and
an estimation unit configured to estimate an amount of the second test substance by applying the trained learning model to the combined sample spectral information,
wherein the learning model is learned by associating learning spectral information generated from the plurality of test pieces of test spectral information selected based on the selected two or more sample pieces with quantitative information specified from the selected two or more test pieces, and
wherein estimated amount is transformed to a display format of a display unit.

* * * * *